US007838236B2

(12) United States Patent
Squirrell

(10) Patent No.: US 7,838,236 B2
(45) Date of Patent: Nov. 23, 2010

(54) ANALYTICAL METHOD AND KIT

(75) Inventor: David James Squirrell, Wiltshire (GB)

(73) Assignee: Enigma Diagnostics Limited, Wiltshire (GB)

( * ) Notice: Subject to any disclaimer, the term of this patent is extended or adjusted under 35 U.S.C. 154(b) by 308 days.

(21) Appl. No.: 12/064,103

(22) PCT Filed: Aug. 8, 2006

(86) PCT No.: PCT/GB2006/002967

§ 371 (c)(1),
(2), (4) Date: Apr. 29, 2008

(87) PCT Pub. No.: WO2007/020384

PCT Pub. Date: Feb. 22, 2007

(65) Prior Publication Data

US 2008/0233588 A1  Sep. 25, 2008

(30) Foreign Application Priority Data

Aug. 19, 2005 (GB) .................................. 0517005.5

(51) Int. Cl.
C12Q 1/68 (2006.01)
(52) U.S. Cl. ......................................................... 435/6
(58) Field of Classification Search ........................ None
See application file for complete search history.

(56) References Cited

U.S. PATENT DOCUMENTS

| 4,735,897 | A | 4/1988 | Vary et al. |
| 4,795,701 | A | 1/1989 | Vary |
| 4,828,979 | A | 5/1989 | Klevan et al. |
| 5,399,491 | A | 3/1995 | Kacian et al. |
| 5,853,990 | A | 12/1998 | Winger et al. |
| 6,090,589 | A | 7/2000 | Dimond et al. |
| 6,159,693 | A | 12/2000 | Shultz et al. |
| 6,287,891 | B1 | 9/2001 | Sayyah |
| 6,436,355 | B1 | 8/2002 | Lee et al. |
| 6,723,507 | B1 | 4/2004 | Lee et al. |
| 6,833,257 | B2 | 12/2004 | Lee et al. |
| 7,252,975 | B2 | 8/2007 | Squirrell et al. |
| 2005/0112647 | A1 | 5/2005 | Lee et al. |
| 2007/0243553 | A1* | 10/2007 | Squirrell et al. ................. 435/6 |
| 2008/0118921 | A1* | 5/2008 | Tisi et al. ........................ 435/6 |
| 2009/0053728 | A1 | 2/2009 | Squirrell et al. |

FOREIGN PATENT DOCUMENTS

| EP | 0212067 | A1 | 3/1987 |
| EP | 0254646 | A1 | 1/1988 |
| EP | 0524448 | A1 | 1/1993 |
| EP | 0639647 | A2 | 2/1995 |
| EP | 0810030 | A1 | 12/1997 |
| WO | 8800593 | A1 | 1/1988 |
| WO | 9525798 | A1 | 9/1995 |
| WO | 9602665 | A1 | 2/1996 |
| WO | 9804738 | A1 | 2/1998 |
| WO | 9824548 | A1 | 6/1998 |
| WO | 9914336 | A2 | 3/1999 |
| WO | 9928500 | A1 | 6/1999 |
| WO | 9928501 | A1 | 6/1999 |
| WO | 9942611 | A1 | 8/1999 |
| WO | 9946409 | A1 | 9/1999 |
| WO | 9966071 | A1 | 12/1999 |
| WO | 0022165 | A1 | 4/2000 |
| WO | 0023878 | A2 | 4/2000 |
| WO | 0049179 | A1 | 8/2000 |
| WO | 0120002 | A1 | 3/2001 |
| WO | 0131028 | A2 | 5/2001 |
| WO | 0229085 | A2 | 4/2002 |
| WO | 02090586 | A2 | 11/2002 |
| WO | 03087388 | A2 | 10/2003 |
| WO | 2004076691 | A1 | 9/2004 |
| WO | 2007020384 | A1 | 2/2007 |

OTHER PUBLICATIONS

Donis-Keller, "Site specific enzymatic cleavage of RNA"; Nucleic Acids Research, 1979, pp. 179-192; vol. 7, No. 1.
Evans et al., "The Mechanism of the Pyruvate Phosphate Dikinase Reaction", Biochemistry, 1968, pp. 1448-1453, vol. 61.
Holland et al., "Detection of specific polymerase chain reaction product by utilizing the 5'-3' exonuclease activity of Thermus aquaticus DNA polymerase"; The Proceedings of the National Academy of Sciences, USA, 1991. pp. 7276-7280, vol. 88.
Moyer et al., "Ultrasensitive Assay of RNA: Application to 100-500 Cells", Analytical Biochemistry, 1983, pp. 190-193, vol. 131.
RNAse H Catalog #M0297S; Retrieved from the New England BioLabs, Inc. website on Feb. 24, 2010, 2 pages.
Non-Final Office Action for U.S. Appl. No. 11/772,300 dated Nov. 6, 2008; 8 pages.
Final Office Action for U.S. Appl. No. 11/772,300 dated Dec. 1, 2009; 8 pages.
Eisaki et al., "Pyruvate phosphate dikinase from a thermophilic actinomyces *Microbispora rosea* subsp. *aerata*: purification, characterization and molecular cloning of the gene", Biochimica et Biophysica Acta, 1999, pp. 363-373, vol. 1431.
Notomi et al., "Loop-mediated isothermal amplification of DNA", Nucleic Acids Research, 2000, e63, vol. 28, No. 12.
Sakakibara et al., "An Enzymatic Cycling Method Using Pyruvate Orthophosphate Dikinase and Firefly Luciferase for the Simultaneous Determination of ATP and AMP (RNA)", Analytical Biochemistry, 1999, pp. 94-101, vol. 268.

(Continued)

*Primary Examiner*—Young J Kim

(57) ABSTRACT

Analytical methods using RNA-containing probes for the detection or analysis of nucleic acid sequences is described. These probes are contacted with a sample suspected of containing the nucleic acid sequence and if they form duplexes, they are hydrolysed. This may be done, for example during an amplification reaction. AMP generated as a result of the hydrolysis is converted to ATP. The ATP may then be detected using bioluminescent reagents. Inclusion of modified adenosine in at least one probe means that the signal arising from one probe will give rise to a different and distinguishable bioluminescent signal thus enabling the use of for example an internal control in bioluminescently-reported nucleic acid tests.

35 Claims, 1 Drawing Sheet

OTHER PUBLICATIONS

Figure 1:
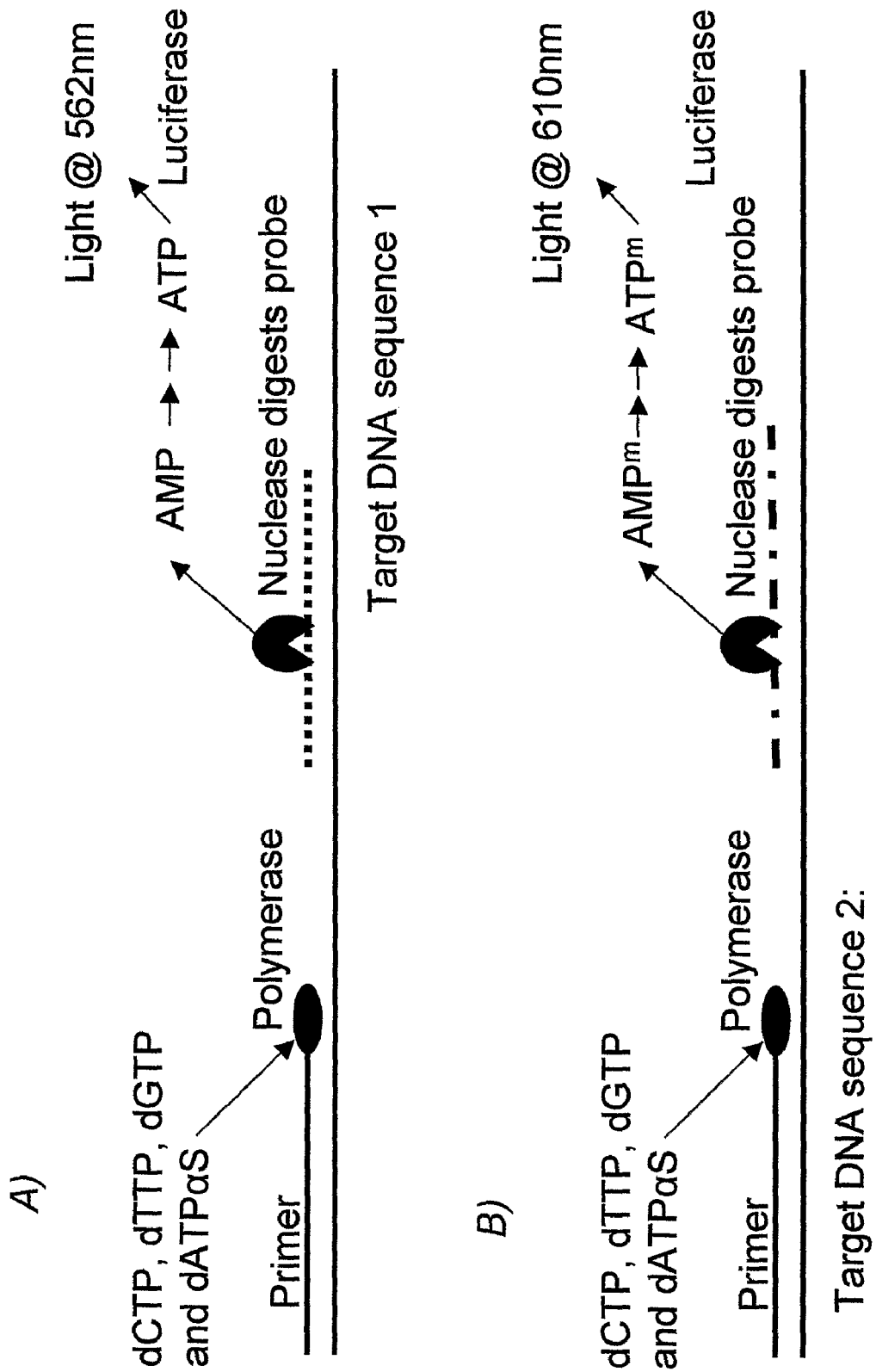

Walker et al., "Isothermal in vitro amplification of DNA by a restriction enzyme/DNA polymerase system", Proceedings of the National Academy of Sciences USA, 1992, pp. 393-396, vol. 89.

GB Search Report for Application No. GB0517005.5, dated Dec. 19, 2005, 1 page.

International Search Report for PCT/GB2006/002967, dated Oct. 10, 2006, 4 pages.

Cooper et al., "The Direct Synthesis of Phosphoenolpyruvate from Pyruvate by *Escherichia coli*", Proceedings of The Royal Society, 1967, vol. 168, No. 1012, Abstract only.

Office Action of U.S. Appl. No. 11/772,300 dated Apr. 10, 2010, 16 pages.

\* cited by examiner

ANALYTICAL METHOD AND KIT

The present invention relates to a method of analysing a nucleic acid sequence, for example to detect the presence of a particular sequence within a sample, or to determine the precise sequence of a particular nucleic acid, and to kits and reagents for use in these methods.

Currently there is a wide range of methods for conducting the analysis of nucleic acids. Analytical methods may be directed to those that detect the presence or amount of a particular nucleic sequence in a sample suspected of containing that sequence. Other methods elucidate the structure of a nucleic acid to determine its sequence of nucleotides for information or diagnostic purposes.

Amplification reactions are commonly used to effect or assist in this analysis, particularly where the particular nucleic acid sequence is present in only minute amounts. The use of amplification reactions such as the polymerase chain reaction (PCR) for detection of target nucleic acid sequences is well known. One or more primers which are specific for the particular sequence are included in an amplification reaction mixture. These will hybridise to the specific target sequence when in single stranded form within a sample tube. If the target sequence is present, the primer will bind to it, whereupon polymerase enzyme present in the mixture will, at certain temperature conditions, extend the primer to form a complete complementary strand. This material then forms further templates, for amplification in subsequent cycles of denaturation, primer annealing and extension.

Isothermal amplification techniques are also known, and these include Strand Displacement Amplification (SDA) (Walker et al. Proc. Natl. Acad. Sci. USA (1992) 89, 392-396), loop-mediated isothermal amplification (LAMP) (Notomi et al. Nucleic Acids Res. 28, 2000) where the polymerase used has strand displacement activity, rolling circle amplification (RCA), etc.

The amplified product may be detected, for example on an electrophoretic gel. However, fluorescent labelling methods are now frequently used to detect when an amplification reaction has been effected, and/or to monitor its progress. Examples of such assays include the TAQMAN™ assay, as well as assays described and claimed for example in WO 99/28500, WO 99/28501, WO 99/42611 and WO 99/66071. An assay using labelled ribo-oligonucleotide probes is described in WO 98/04738. Labelling of probes however is a complex process which increases the cost.

Methods for sequencing nucleic acid sequences are also well known. Gel methods are conventional. More recent methods are carried out using devices such as the Pyrosequencer available from Biotage AB, that rely on the generation of a bioluminescent signal when a correct nucleotide is added during the construction of a complementary strand on a single stranded nucleic acid template. Other methods for interrogating the identity of a specific base in a nucleic acid sample using pyrophosphorolysis reactions are described in WO 99/46409.

WO 02/090586 describes how ribonucleic acid (RNA) probes, which are unlabelled, can provide a useful means for monitoring or detecting such events. The detection in this case relies on the hydrolysis of specific probes, followed by detection of adenosine monophosphate (AMP) produced by the hydrolysis. In particular, AMP produced as a by-product of probe hydrolysis is phosphorylated to form adenosine triphosphate (ATP), which can then be detected, for instance using a bioluminescent signalling system such as the luciferase/luciferin system.

Bioluminescent signalling systems are particularly preferred because they are generally more sensitive and provide a greater dynamic range than fluorescent systems. Consequently, the use of RNA hydrolysis probes in analytical methods facilitates the detection of interactions at the nucleic acid level within a sample and so gives rise to enhanced methods of analysis.

In addition, the apparatus required to detect a bioluminescent signal is simpler than that required to detect a fluorescent signal. A light detector such as a CCD camera can detect a bioluminescent signal whereas a filtered collimated light source and an optical system are required in addition to a detector in order to measure a fluorescent signal.

However, although fluorescent signalling systems can be used in multiplex assays, by the use of different fluorescent dyes or the like on various probes, the system described in WO 02/090586 is not suitable for use in multiplex assays. This is because the signalling relies on the production of AMP, which is ubiquitous in the hydrolysis of all probes.

Furthermore, when using such a system, there has hitherto been no possibility of utilising internal controls. For instance, internal control reactions are generally similar reactions to the test reaction, but with a different target sequence. They are run simultaneously in a reaction vessel with a test reaction such as an amplification reaction. An example of such a reaction is described in U.S. Pat. No. 6,723,507. The target of the internal control reaction is known to be present in the reaction vessel throughout and its amplification is used to verify that an assay has functioned, particularly if the assay correctly provides a negative result with respect to the target of the test. The internal control provides assurance that an assay has functioned so that false negative results can be eliminated.

When using AMP as the basis for a signalling system however, no internal control is possible since the signal it produces is going to be the same irrespective of the source.

The applicants have found a way of addressing this problem, which allows the advantageous bioluminescent system to be applied in multiplex assays, and/or to be subject to an internal control.

According to the present invention there is provided a method for detecting more than one nucleic acid sequence in a sample, said method comprising:

contacting said sample with a first RNA-containing probe which is capable of hybridising to a first nucleic acid sequence, and a second RNA-containing probe which is capable of hybridising to a second nucleic acid sequence, wherein at least one adenosine in said first or said second RNA-containing probe is a modified form of adenosine, which, when phosphorylated to the corresponding triphosphorylated form, interacts with a bioluminescent signalling system to produce an altered bioluminescent signal as compared to the signal produced by said bioluminescent signalling system when it interacts with non-modified adenosine in triphosphorylated form; under conditions such that the first RNA-containing probe will bind to any first nucleic acid sequence present in the sample, and the second RNA-containing probe will bind to any second nucleic acid sequence present in the sample, subjecting any nucleic acid/probe complex to conditions under which RNA-containing probe bound to nucleic acid is hydrolysed to generate adenosine monophosphate (AMP), and/or modified adenosine monophosphate (AMP$'''$), phosphorylating any AMP and AMP$'''$ present to produce adenosine triphosphate (ATP) or modified adenosine triphosphate (ATP$'''$) respectively, detecting ATP or ATP$^m$ using a bioluminescent signalling system which produces a different signal when reacting with ATP$^m$ as compared to ATP, determining the nature of the signal so produced and relating this to the presence or absence of said first nucleic acid and said second nucleic acid in the sample.

For the avoidance of doubt, the expression "modified form of adenosine" as used herein means that the structure of the adenosine is altered but it may still be phosphorylated in a way which is similar to adenosine, but when it is phosphorylated to the corresponding triphosphorylated form, it interacts with a bioluminescent signalling system to produce an altered bioluminescent signal as compared to the signal produced by said bioluminescent signalling system when it interacts with unmodified adenosine in triphosphorylated form. The molecule will still be recognisable as an adenosine derivative in that it will contain a purine ring linked to a sugar molecule. However, it will generally not contain other modification moieties such as biotin etc.

As used herein, the expression "RNA-containing probe" relates to nucleic acid sequences which comprise at least some RNA. Thus it includes RNA/DNA heteropolymers which contain at least one adenosine nucleotide or a modified form of adenosine as described above, as well as RNA molecules. For instance, the probe could comprise essentially a DNA polymer wherein one or more deoxy-adenosine nucleotides are replaced by adenosine or a modified form of adenosine, also as described above, or the probe could contain a stretch of DNA or admixed DNA/RNA bases with an RNA or modified RNA tail.

In one embodiment, the probes are RNA molecules.

However, in another embodiment, the probe is an RNA/DNA heteropolymer as described above. These molecules may be preferred, where for instance enzymes used to hydrolyse the probe are more effective at hydrolysing molecules of this type. Provided some AMP is released during the hydrolysis, a detectable signal will be produced using the method described above.

The sequence of the RNA-containing probes will be such that they hybridise to a particular target nucleic acid.

Probes and specifically RNA-containing probes will hybridise to nucleic acid sequences that are complementary or substantially complementary thereto. Preferably the modified form of adenosine included in said first or said second RNA-containing probe will bind to a thymidine or uridine in the complementary nucleic acid in the same way as an unmodified adenosine by way of Watson-Crick bonding. However, it is possible for the modification to weaken or eliminate this bonding, and provided the probe is of sufficient length and otherwise of significant complementarity, it will still hybridise to the target sequence.

For the avoidance of doubt also, the expression "RNA-containing probe when in double stranded form" as used herein means that the RNA-containing probe is an element of a duplex nucleic acid wherein the other element of the duplex is any nucleic acid, including DNA, RNA or even a further DNA/RNA heteropolymer.

At least one adenosine, suitably more than one, and preferably all of the adenosine nucleosides in one of said first or said second RNA-containing probe is a modified form of adenosine. Similar modified adenosines should be present in only one of the probes, so that hydrolysis of that probe will give rise to a bioluminescent signal, which is different and distinguishable from that of the other probe.

More than two RNA-containing probes can be used in the process of the invention, to detect further nucleic acid sequences, provided that each of the additional probes contains at least one adenosine which is modified differently from those contained in any other probe in the system, and that the different modification leads to a different and distinguishable bioluminescent signal.

RNA-containing probes, including those which incorporate modified adenosine as described above, may be hydrolysed when in double stranded form, in various ways, for example using enzymes or ribozymes. Preferably the probes are hydrolysed enzymatically.

A variety of enzymes may be used, and the selection will depend upon factors such as the precise nature of the probe employed, the conditions under which the assay is being conducted, and whether or not it is conducted in conjunction with other reactions such as an amplification reaction such as the polymerase chain reaction (PCR). These include polymerase enzymes commonly used in PCR reactions such as Taq polymerase as will be discussed in more detail below.

Alternatively or additionally, they may be hydrolysed by RNAse enzymes, which will hydrolyse them only when in double stranded form, for example as an RNA/DNA duplex. Such duplexes may be formed in the course of an amplification reaction such as a PCR reaction, but this is not necessarily the case. Examples of such enzymes include T7 exonuclease (available from BioLabs), snake venom phosphodiesterase (SVPD) (available from Sigma and Amersham Biosciences), RNAse H (available from Epicentre). It is important to ensure however that any enzymes used in this way are free of unwanted activity such as DNAse or RNAse activity which would non-selectively hydrolyse the RNA-containing probes, for example in single stranded form. The property can be tested for using routine methods. For instance, the enzyme may be incubated with a sample of probe prior to use, and then the sample analysed, for example, by gel electrophoresis or any other conventional method which detects differences in size of nucleic acids.

Particularly preferred enzymes are T7 exonuclease and SVPD. However, in any particular circumstances, enzymes may be tested using routine procedures such as those outlined above, to ensure that they hydrolyse the RNA-containing probe when in double stranded form sufficiently well to ensure that at least some free AMP or AMP$^m$ is released.

Adenosine monophosphate (AMP) or modified adenosine monophosphate (AMP$^m$) obtained by hydrolysis of the first or second nucleic acid probes may be phosphorylated to adenosine triphosphate (ATP) or modified adenosine triphosphate (ATP$^m$) respectively, enzymatically either directly or by way of the production of adenosine diphosphate.

The one or more enzymes necessary to convert AMP or AMP$^m$ produced to ATP or ATP$^m$ respectively (for example as used in (c) below, may for example be selected from phosphoenolpyruvate synthase which produces ATP directly from AMP in the presence of phosphate and phosphoenolpyruvate, which are also added as reagents to the reaction mixture. Alternatively, a combination of a nucleoside triphosphate-adenylate kinase and NTP will yield adenosine diphosphate (ADP) or modified adenosine diphosphate (ADP$^m$) respectively, which may then be converted to ATP or ATP$^m$ respectively by inclusion or addition of an enzyme such as adenylate kinase. (NTP may be present in the reaction mixture anyway, if for example it is used in connection with a polymerase chain reaction).

Yet further examples of suitable enzymes include pyruvate phosphate dikinase such as that described by Eisaki et al, Biochim. et Biophys Acta 1431 (1999) 363-373.

ATP or ATP$^m$ may be readily detected using bioluminescent systems. One of the commonest bioluminescent signalling systems utilises a combination of the enzyme luciferase, found in nature in organisms in particular Coeleoptera such as fireflies and glow-worms, and the enzyme substrate, luciferin. In the presence of adenosine triphosphate (ATP) found in all cells, luciferase oxidises luciferin to produce oxyluciferin and AMP as well as a bioluminescent signal, which may be monitored for example using a luminometer.

The signalling reaction can be represented as follows:

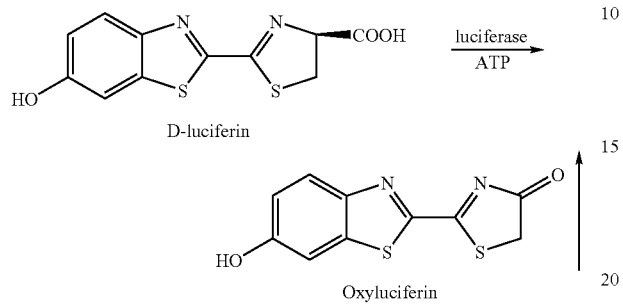

D-luciferin

Oxyluciferin where the vertical arrow indicates a bioluminescent signal. $CO_2$ and AMP are the other reaction products (or $AMP'''$ where $ATP'''$ is the substrate for the luciferase).

Examples of the application of such detection systems are described for example in WO 96/02665, the content of which is incorporated herein by reference.

Thus particularly suitable bioluminescent reagents, which react to the presence of ATP, include luciferin and luciferase. The luciferase used may preferably be a recombinant luciferase which produces a similar effect on a substrate, for example a luciferase which has enhanced thermostability as compared to the native forms. Particular examples of such forms are described for example in EP-A-0524448, WO95/25798, WO99/14336, WO00/23878. WO01/20002 and WO01/31028.

These reagents may be accompanied if necessary by a source of magnesium ions such as magnesium acetate. However, again such salts may be present in the reaction mixture anyway, for example if they are required in the course of an amplification reaction such as the polymerase chain reaction.

In generating a signal, these reagents regenerate an AMP or $AMP'''$ molecule, which in the presence of the enzymes and/or reagents which phorphorylate AMP or $AMP'''$ to ATP or $ATP'''$, these will be reconverted back to ATP or $ATP'''$. Thus the signal builds up exponentially and so will be readily and rapidly detected. An example of such a system is described by Sakakibara et al., Analytical Biochemistry, 268, 94-101 (1999). This exponential rise in signal may mean that detection can be carried out directly, in circumstances where amplification reactions may previously have been required.

When ATP catalyses the luciferase/luciferin reaction system, the resultant signal is a yellow-green signal at about 562 nm. However, it has now been found that certain modified forms of ATP ($ATP'''$) such as deoxy adenosine triphosphate (dATP), will still catalyse the reaction, but that the bioluminescent signal produced is at a longer wavelength for instance, a red signal at about 610 nm-620 nm, and at a much lower level (for example about 1% of the activity of ATP in the assay). This signal, even though at a lower level, can be detected using suitable filters on the light being observed.

The structure of ATP and dATP are as follows:

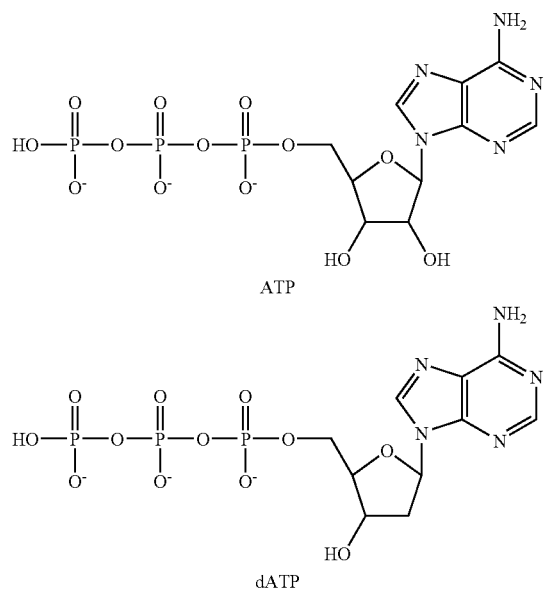

ATP dATP

Other modified adenosines can be employed.

The wavelength of the signals produced can be read using a conventional luminometer, suitably provided with wavelength selective filters, or a sensitive spectrofluorimeter (operated with the light-source switched off) which can distinguish signals at different wavelengths. Production of a signal characteristic only of an unmodified ATP catalysed luciferase/luciferin reaction will indicate that only the probe which did not contain modified adenosine was hydrolysed during the assay, and that therefore only the nucleic acid sequence to which this probe hybridised was present in the reaction mixture. However, any difference in the wavelength of the emitted light will indicate that at least some of the probe which contains a modified adenosine has been hydrolysed, and that therefore the sample contains some of the nucleic acid sequence to which this probe hybridises.

In a particularly preferred embodiment, the method of the invention is used in conjunction with an amplification reaction such as the polymerase chain reaction or an isothermal amplification reaction such as those mentioned above, to detect sequences which are present in only small quantities in the original sample.

It may be applied for example as an end-point assay, where the first and second RNA probes together with the enzymes or reagents necessary to bring about hydrolysis of annealed probes, and phophorylation of AMP or $AMP'''$ are added with the bioluminescent reagents at the end of an amplification reaction, and the resultant mixture subjected to conditions suitable for the assay to be conducted as described above.

Alternatively however, these reagents are present throughout the amplification reaction, allowing the possibility that the signal can be generated simultaneously with the amplification.

For instance, where the RNA-containing probes are present throughout the amplification, the probes may be designed to anneal to their respective target sequence during the annealing phase of the amplification process. Suitably the polymerase used in the amplification reaction is one which hydrolyses the RNA-containing probe when in double stranded form. In this case, the reaction can be designed so that probes will be at least partially hydrolysed during the extension phase, resulting in a build up in AMP or AMP$^m$ and subsequently, after phosphorylation, ATP or ATP$^m$ for detection.

Examples of suitable DNA polymerases which may be used in the context of a conventional PCR reaction are thermostable polymerases such as *Thermus aquaticus* polymerase (Taq), *Thermus thermophilus* polymerase (Tth), *Thermus* species NH polymerase (TspNH), *Thermus brockianus* polymerase (Tbr) (all obtainable for example from GeneSys Limited, Farnborough, U.K.), *Pyrococcus furiosus* polymerase (Pfu) (obtainable from Stratagene), 9°N7 exo- DNA polymerase, and *Thermococcus litoralis* DNA polymerase (obtainable from New England Biolabs as VENT™ DNA polymerase).

If however, the polymerase used does not hydrolyse the RNA-containing probe quickly enough, for example if rapid PCR is being employed, or if it does not fully hydrolyse the probe to the extent that single nucleotides include AMP or AMP$^m$ are released, then an additional hydrolytic enzyme may be added to digest small fragments released by the polymerase to free nucleotides including AMP. Examples of such enzymes include those listed above, such as T7 exonuclease or SVPD.

When such hydrolytic enzymes are used, it may be preferable to modify each probe so that it is not hydrolysed by these enzymes in the free state. For instance, where the enzymes have 5'-3' exonuclease activity against small single stranded fragments, then the probe is suitably blocked at the 5' end. At the 3' end blocking may be even more necessary since in addition to preventing unwanted 3'-5' exonuclease activity, the probes may also need to be blocked to prevent extension by polymerase activity. Suitable blocking methods are well known in the art. For instance, the 3' hydroxy moiety can be chemically modified, for example by introduction of a phosphate group, to block the extension.

Such amplification reactions should be conducted in the absence of any form of ATP which reacts significantly with the bioluminescent signalling system. Certain amplification reactions such as the PCR reaction may require, for efficient operation of the polymerase, to be carried out in the presence of a form of ATP such as deoxyATP (dATP). Clearly such reagents cannot be included where any of the probes utilised during the method described above includes similarly modified adenosines as this would lead to false positive results. In such cases, it may be necessary to use alternative forms of dATP, preferably a form which, although acting as a substrate for the DNA polymerisation, does not have any significant activity in the bioluminescent reaction. A particular example of suitable alternative forms may be 2'-deoxyadenosine-5'-O (1-thiotriphosphate (dATPαS) or 7-deaza-2'-deoxyadenosine-5'-triphosphate (c7dATP), the structures of which are as follows:

dATPαS

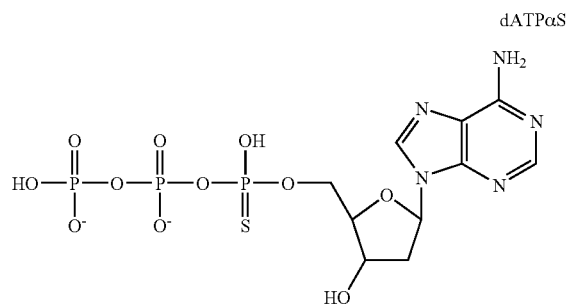

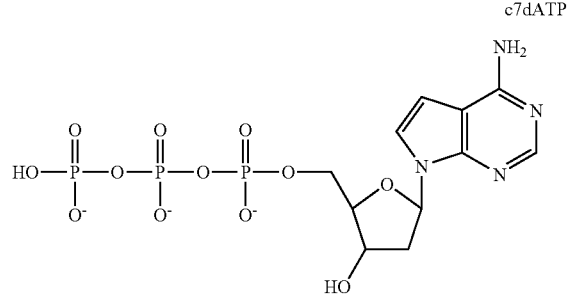

c7dATP

These molecules support polymerase activity in a PCR, but interact in the bioluminescent system only at very high levels such as in the nanomolar concentrations as compared to ATP or dATP which produce detectable signals in the picomolar concentration range (J. Eriksson, Doctoral Thesis, Advancements [sic] in Firefly Luciferase-Based Assays and Pyrosequencing Technology, KTH, Stockholm, Sweden, 2004). As a result, they can be included in the reaction mixture at levels which support the PCR, but do not at those levels, generate a bioluminescent signal of sufficient intensity or wavelength to interfere with that produced as a result of probe hydrolysis.

In this way, any signal resulting from the presence of any alternative form of ATP added to the reaction mixture for other purposes, such as the conducting of the PCR, would not interfere with the signal produced as a result of hydrolysis of the RNA-containing probe.

The polymerase chain reaction utilising the above-described method may comprise a multiplex PCR where more than one sequence is amplified, for example a target sequence and an internal control sequence which is added to the reaction mixture prior to amplification. In such cases, it may be appropriate to add two sets of reaction primers, one set applicable to each sequence to be amplified, as would be understood in the art. However, where the first and second probes anneal to different forms of a similar sequence, for example, to different allelic forms, a single set of primers may be sufficient to cause amplification of both forms.

The bioluminescent reagents may be added at the end of the amplification in order to carry out an end-point detection procedure. It is possible however for them to be present or added throughout the amplification reaction so that the progress of the reaction can be monitored.

Preferred forms of luciferase used in the methods may be those which have higher levels of thermostability than the wild-type. Particular examples of such enzymes are described for example in EP-A-0524448, WO95/025798, WO99/14336, WO00/24878, WO01/20002 WO01/31028, the content of which is incorporated herein by reference. The wavelength of emission of some of these enzymes differs from that of the wild-type enzymes. However, provided they produce distinguishable signals when activated by ATP derived by phophorylation of the modified form or adenosine as compared to the ATP derived by phosphorylation of adenosine, they may be used in the method of the invention. This can be tested using routine methods which are conventional in the art.

However, generally speaking, the thermostability of reagents such as luciferase is not sufficient to allow it to be present throughout an amplification reaction which involves thermal cycling such as a PCR reaction. Therefore isothermal amplification reactions may be preferred where continuous monitoring is required. However, it is possible also to adapt a PCR reaction so that the bioluminescent reagent is added at the end of each cycle and the signal produced read at that time, so as to generate monitoring information. Such information may be used then in the quantification of the target nucleic acid sequence in the sample, using algorithms etc. which are known in the art.

The amplification reaction may be conducted in the usual way, for example by cycling the reaction mixture through denaturation, annealing and extension temperatures.

The reactions as described above could be carried out in a variety of conventional equipment. These include for example a Pyrosequencer (available from Biotage AB, Sweden), which is already provided with appropriate signal detection means. Alternatively, the reaction may be carried out using block heating devices as described for example in EP-A-0810030 and supplied by the Perkin-Elmer Corporation, or other types of thermal cycler such as those described in WO98/24548, with the addition of suitable light detection means such as a CCD camera equipped with appropriate filters.

Thus in a further particular embodiment, the invention provides a method for detecting a nucleic acid sequence, said method comprising conducting a polymerase chain reaction in the presence of (a) a first RNA-containing probe which is capable of hybridising to a first nucleic acid sequence during an annealing phase of the polymerase chain reaction, and a second RNA-containing probe which is capable of hybridising to a second nucleic acid sequence also during an annealing phase of the polymerase chain reaction, wherein at least one adenosine in said first or said second RNA-containing probe is a modified form of adenosine, which, when phosphorylated to the corresponding triphosphorylated form, interacts with a bioluminescent signalling system to produce an altered bioluminescent signal as compared to the signal produced by said bioluminescent signalling system when it interacts with adenosine in triphosphorylated form, (b) an enzyme or enzyme mixture which hydrolyses the RNA-containing probe when in double stranded form (for example as an RNA/DNA duplex) and (c) one or more enzymes or reagents necessary to convert adenosine monophosphate to adenosine triphosphate or modified adenosine monophosphate to modified adenosine triphosphate; phosphorylating any AMP and modified adenosine monophosphate present to produce ATP or modified adenosine triphosphate respectively;

adding to the sample bioluminescent reagents which react to the presence of ATP and to said modified ATP in a different and distinguishable way, and determining the nature of the signal so produced and relating this to the presence or absence of said first nucleic acid and said second nucleic acid in the sample.

This method is illustrated diagrammatically hereinafter in FIG. 1.

A sample which contains or is suspected of containing two particular nucleic acid sequences, "Target DNA sequence 1", and "Target DNA sequence 2" (which might be an control sequence which is amplified using the same primers as Target DNA sequence 1) subjected to a PCR, which is carried out with added dNTPs, but in this case dATP has been replaced with dATPαS.

A different RNA-containing probe specific for each target sequence is present. The probes contain either contain A) AMP bases or B) modified AMP bases (AMP$^m$) such as dAMP bases which, after binding-dependent hydrolysis and enzymatic phosphorylation, interact with luciferase to yield distinguishable signals.

During the DNA polymerisation step of the PCR reaction, which is illustrated in FIG. 1, both primers and complementary RNA-containing probes bind to the target sequences.

Nucleases, which may include the polymerase enzyme, where this is one which has 5' to 3' nuclease activity such as Taq polymerase, then operate to hydrolyse the RNA-containing probes as illustrated by the dashed line, releasing AMP in the case of the first reaction (A) and dAMP in the case of the second reaction (B). AMP is then is converted in situ to ATP, whereas AMP$^m$, as dAMP, is then is converted in situ to dATP. Both ATP and dATP can be detected as a light signal following addition of bioluminescent reagents such as luciferin and luciferase.

However, the wavelength of the light produced by the ATP will be different to that produced by dATP. The first reaction, with normal adenosine bases in the RNA-containing probe, will give rise to the emission of green light at a wavelength of about 562 nm under these conditions. If the second reaction has proceeded, the modified adenosine bases in the RNA-containing probe, will give rise to the emission of light of a different wavelength, for instance in the case of dAMP, the ultimate signal will comprise red light at a wavelength of about 610 nm. Therefore the presence of one or both of the target sequences can be determined by analysing the wavelength of the emitted light.

At the same time the polymerase activity will ensure that the PCR proceeds, although where the ATP$^m$ is dATP, some of this will be incorporated into the resultant DNA product as a side reaction.

The methods described above can be used to determine whether a particular sample contains one or more specific nucleic acid sequences.

For instance, the method could be utilised wherein the presence of different sequences, for example those derived from different organisms, for example, microorganisms such as bacteria or viruses, are suspected. Using a first RNA-containing probe which is specific for a nucleic acid sequence found in a first organism and a second RNA-containing probe which is found in a second organism will mean that the bioluminescent signal produced will allow the presence of absence of one or both of these organisms to be determined. This may be useful in hygiene applications as well as in clinical diagnosis.

For instance, it may be used to analyse a genetic sample for the presence of a specific genotype, polymorphism etc. In this case, the first nucleic acid will be one form of a particular gene, and the second nucleic acid will be an alternative form. When a sample is homozygous or a particular form of the gene, then only the first or second probe will by hydrolysed. Where this probe does not contain a modified adenosine, the bioluminescent signal detected will be characteristic only of ATP. Similarly, where the sample is homozygous for the other form of the gene, then the bioluminescent signal measured will be characteristic only of the hydrolysis of the probe containing modified adenosine. Preferably all of the adenosines in this probe will be modified so a signal of a single wavelength will be detected. However, it is possible that "mixed" signals can be determined, whereby light of different wavelengths is emitted and detected using a system of optical filters or the like. Such as system would be required where the sample is heterozygous for the gene type.

Where the method of the invention is used in conjunction with an amplification reaction such as a PCR, it may be desirable to link the RNA-containing probe to a DNA sequence which acts as a primer to the reaction by way of a "blocking group" which is suitably a chemical linker or non-amplifiable monomer such as hexethylene glycol and which prevents an extension reaction amplifying the probe region of the olignucleotide. The linker will further prevent hydrolysis of the probe from extending along the primer.

Probe/primer combinations of this general type are well known as "Scorpions" and these are described for instance in WO 99/66071.

With conventional Scorpion™ probes, sequence-specific priming and PCR product detection is achieved using a single oligonucleotide. The Scorpion™ probe maintains a stem-loop configuration in the unhybridized state. A pair of interacting fluorophores is attached to the oligonucleotide; for example a fluorophore at the 5' primer end of the oligonucleotide is quenched by a moiety coupled to the 3' probe end. The probe section contains sequence that is complementary to the extension product of the primer. After extension of the Scorpion™ primer, the specific probe sequence is able to bind to its complement within the extended amplicon thus opening up the hairpin loop. This prevents the fluorescence from being quenched and a signal is observed.

For use in the method of the present invention, the single oligonucleotide probe/primer need not carry any specific signalling moieties such as fluorophores, as the signal is generated as a result of the hydrolysis of the probe section. This will reduce the cost and difficulty in preparation. Additionally, it needs only to be modified to the extent that the probe section comprises a RNA-containing probe as defined above. The RNA-containing probe will include adenosine or modified adenosine as required for the operation of the process.

Such primer/probe combinations are novel and form a further aspect of the invention.

The method of the invention may also be adapted for sequencing applications and/or for detecting polymorphisms or variations in DNA or RNA sequences.

In a further aspect, the invention provides a method for determining the sequence of a nucleic acid, said method comprising (i) binding a first and a second RNA-containing probe to a known region of said sequence such that at least one nucleotide at an end of said probes reaches into an unknown or uncertain region of the sequence and wherein the first and second RNA-containing probes differ by the nucleoside found at the said end thereof, and wherein at least one adenosine in said first or said second RNA-containing probe is a modified form of adenosine, which, when phosphorylated to the corresponding triphosphorylated form, interacts with a bioluminescent signalling system to produce an altered bioluminescent signal as compared to the signal produced by said bioluminescent signalling system when it interacts with adenosine in triphosphorylated form;

(ii) hydrolysing the RNA-containing probes using an enzyme which hydrolyses said RNA-containing probe when in double stranded form (for example as an RNA/DNA duplex);

(iii) converting adenosine monophosphate produced to adenosine triphosphate (ATP) and modified adenosine monophosphate($AMP^m$) to modified adenosine triphosphate ($ATP^m$);

(iv) adding to the sample bioluminescent reagents which react differently to the presence of ATP and $ATP^m$;

(v) detecting a signal from said bioluminescent reagents; and (vi) relating that signal to the presence of a region of the sequence which is complementary or otherwise to the end of one of the said probes.

In such cases, if the one or more nucleotides at the end of the probe are precisely complementary to the unknown or uncertain sequence, the probe will bind most efficiently to it, whereupon the enzyme will efficiently hydrolyse the bound probe during step (ii). As a result, AMP, or $AMP^m$ is generated depending upon which probe hydrolyses in this way, and this is converted to ATP or $ATP^m$ respectively as described above, and detected using a bioluminescent system.

However, if the nucleotide(s) at an end of the RNA-containing probe is not a correct match for the template DNA, then the effect of the enzyme in (ii) will be to largely dislodge the probe intact, from the template. As a result no significant hydrolysis occurs and this will be reflected in the lack or substantial reduction in bioluminescent signal generated from said probe.

This reaction may be carried out using probes with different nucleotides at the end regions simultaneously, or if desired, more than once. For example, if the nucleotide found within the sequence at this position is not known, four different probes, each with a different nucleotide C, G, U and A at the end may be prepared. If possible, each probe would include a different form of adenosine, three of which are suitably modified and one of which is not. Alternatively, two of the probes can be prepared with modified adenosine, and the reaction conducted twice, each time with one probe with modified adenosine and one probe with unmodified adenosine.

By conducting these reactions, it should be readily apparent which is the correct nucleotide at this position, by the level of the signal generated. A good signal would be expected only in the reaction in which the probe includes the complementary nucleotide at the end.

If desired, more than one unknown nucleotide may be included at the end, for example up to three nucleotides. In such cases, probes representing all possible combinations of sequences at the positions may be carried out. It would be expected that the probe which had a precisely complementary sequence at the end would be efficiently hydrolysed.

The end used may be the 3' or the 5' end of the probe, depending upon the nature of the known versus the unknown or uncertain sequence. The enzyme used in step (ii) will be selected with this in mind. Hydrolysis of a tightly bound RNA-containing probe may be better effected when the end is the 5' end and the enzyme used in step (ii) is capable of 5'-3' hydrolysis (as compared to 3'-5' hydrolysis), as often found in enzymes which are regarded as having good "proof-reading" function.

The enzymes and reagents used in the method will be similar to those used in the method for detecting the presence or amount of a nucleic acid sample as described above. Similarly the reaction may be carried out in equipment as described above.

The sequencing reaction may be used in conjunction with an amplification reaction such as a PCR reaction. For example the reaction may be carried out subsequent to a PCR reaction. At least some stages of the PCR reaction may be effected in order to achieve the hydrolysis in step (ii). However, generally speaking this may not be necessary, since the system itself provides a good amplified signal, as a result of the "recycling" of the AMP detected.

Such methods would be useful in sequencing, where at least a portion of the starting sequence is known (for example a universal priming sequence). Entire sequences can then be resolved, by reiterating the process along the length of the sequence. Parallel reactions to elucidate the sequence may be possible using RNA oligonucleotide libraries as the probes, where for example the sequence is known to contain several conserved regions along its length, for example as occurs during ribotyping. These regions may each be used as the known sequence for locating the RNA-containing probes.

Sequencing the reverse direction by way of confirmation may also be carried out using the method described above. Where possible as a result of the presence of conserved regions, this may be done in parallel using an array of reactions.

Alternatively, the methods may be used in the detection of polymorphisms or allelic variations for use in diagnostics. In such cases, the sequence may be broadly known except for a small region of one or more nucleotides which may be uncertain at the locus of the polymorphism or variation. In such cases, the RNA-containing probe is designed such at least an end region nucleotide corresponds to the polymorphism or variation in the sequence, whereupon efficient hydrolysis or otherwise, will indicate whether or not the actual sequence is complementary to the probe sequence or not.

The reactions described above, including detection, amplification and sequencing reactions, may be conducted in reaction tubes, wells or vessels as appropriate and as known in the art.

Where a plurality of reactions as described above, for example amplification or sequencing reactions are carried out, these may suitably be carried out simultaneously in separate reaction tubes, wells or vessels, which are arranged in an array. The tubes, wells or vessels may be thermally cycled (or isothermally incubated, depending upon the nature of the process being employed) together, and the signals from each tube monitored using an appropriately configured luminometric system.

Alternatively, probes may be immobilised on a support, for example of the "dipstick" design or a slide or chip, to provide a diagnostic test, for example for a polymorphism or allelic variation in a particular test sequence as outlined above.

In yet a further aspect, the invention provides a kit for use in a method as described above. Such kits will comprise at least two RNA-containing probes, which are specific for the target sequences, and wherein one of which includes at least one modified adenosine as described above.

Kits may also optionally also comprise means for converting AMP to ATP, or $AMP^m$ to $ATP^m$. Particular examples of such means are the enzymes listed above for use in this context.

In the case of the method of detecting polymorphisms, the kit may comprise up to four similar RNA-containing probes, which differ only by the presence of a different nucleotide at the 3' end. In this case, different modified adenosines will be present in at least three of said probes.

Kits will suitably comprise one or more further reagents for use in the method. In particular, they may also contain bioluminescent reagents such as luciferase and/or luciferin. Suitably the luciferase is a recombinant thermostable luciferase as described above.

Other particular optional components of the kit may include one or more set of primers for use in a particular amplification or amplifications. As described above, a primer may be linked to an RNA-containing probe by way of a blocking group as described above, so that they form a single oligonucleotide.

In addition, kits may contain one or more enzymes (for example as an enzyme mixture) which are able to hydrolyse RNA-containing probes bound to nucleic acid to generate adenosine monophosphate (AMP), and/or modified adenosine monophosphate ($AMP^m$). Examples of such enzymes include DNA polymerase which hydrolyses the RNA-containing probes or other hydrolytic enzymes such as an RNAse as described above.

Other reagents such as buffers, nucleotides, polymerase enzymes etc., which might be required in order to effect an amplification may also be included.

RNA-containing hydrolysis probes therefore provide a very versatile means for generating signals indicating the presence of very specific nucleic acid sequences within a sample. The sensitivity of assays using such probes combined with bioluminescent detection systems is high and signals can be generated rapidly.

RNA-containing probes which include a modified adenosine as described above are also novel and form a further aspect of the invention.

RNA-containing probes as described above, which are either RNA molecules containing a modified form of adenosine, or a DNA/RNA heteropolymer as described above are novel and form a further aspect of the invention. Furthermore, the use of these probes individually in an assay for particular nucleic acid sequences, in which they are hydrolysed to release AMP or $AMP^m$ which is phorphorylated to ATP or $ATP^m$ and detected using a bioluminescent system, forms a yet further aspect of the invention.

The invention claimed is:

1. A method for detecting more than one nucleic acid in a sample, said method comprising:
    contacting said sample with a first RNA-containing probe which is capable of hybridising to a first nucleic acid and a second RNA-containing probe which is capable of hybridising to a second nucleic acid, wherein at least one adenosine in said first or said second RNA-containing probe is a modified form of adenosine, the contacting occurring under conditions such that the first RNA-containing probe will bind to any first nucleic acid present in the sample, and the second RNA-containing probe will bind to any second nucleic acid present in the sample,
    subjecting any nucleic acid/probe complex to conditions under which RNA-containing probe bound to nucleic acid is hydrolysed to generate adenosine monophosphate (AMP) and/or modified adenosine monophosphate ($AMP^m$),
    phosphorylating any AMP and $AMP^m$ present to produce adenosine triphosphate (ATP) or modified adenosine triphosphate ($ATP^m$) respectively,
    detecting ATP or $ATP^m$ using a bioluminescent signalling system which produces a different signal when reacting with $ATP^m$ as compared to ATP, and
    determining the nature of the signal so produced and relating this to the presence of said first nucleic acid and said second nucleic acid in the sample.

2. The method according to claim 1, wherein the phosphorylating occurs enzymatically.

3. The method according to claim 1, wherein the first and second RNA-containing probes are RNA molecules.

4. The method according to claim 1, wherein the first and second RNA-containing probes are RNA/DNA heteropolymers.

5. The method according to claim 1, wherein more than one adenosine in one of said first or said second RNA-containing probes is a modified form of adenosine.

6. The method according to claim 1, wherein the modified adenosine is deoxyadenosine.

7. The method according to claim 1, wherein the RNA-containing probes bound to nucleic acids are hydrolysed using an enzyme.

8. The method according to claim 7, wherein the enzyme is selected from the group consisting of polymerase enzymes, RNAse enzymes, and combinations thereof.

9. The method according to claim 7, wherein the enzyme is an RNAse.

10. The method according to claim 7, wherein the enzyme is T7 exonuclease or snake venom phosphodiesterase.

11. The method according to claim 1, wherein AMP or AMP$^m$ obtained by hydrolysis of the first or second RNA-containing probes is phosphorylated to ATP or ATP$^m$ using at least one hosphorylating enzyme.

12. The method according to claim 11, wherein the phosphorylating enzyme is selected from the group consisting of phosphoenolpyruvate synthase, a nucleoside triphosphate-adenylate kinase and NTP, and pyruvate phosphate dikinase.

13. The method according to claim 1, wherein the bioluminescent signalling system comprises luciferase, and luciferin.

14. The method according to claim 1, wherein the first and second RNA-containing probes are modified to ensure that they are not hydrolysed when in the free state.

15. The method according to claim 14, wherein the RNA-containing probes are chemically blocked at the 5' end.

16. The method according to claim 1, which is conducted in conjunction with a nucleic acid amplification reaction.

17. The method according to claim 16, wherein the amplification reaction is an isothermal reaction.

18. The method according to claim 17, wherein first and second RNA-containing probes, at least one agent for hydrolysis, at least one agent for phosphorylation, and the bioluminescent signalling system are present throughout the amplification reaction.

19. The method according to claim 16, wherein the amplification reaction is a polymerase chain reaction.

20. The method according to claim 19, wherein first and second RNA-containing probes, at least one agent for hydrolysis, and at least one agent for phosphorylation are present throughout the amplification reaction.

21. The method according to claim 20, wherein the agent for hydrolysis comprises a DNA polymerase used to effect the polymerase chain reaction reaction.

22. The method according to claim 21, wherein the agent for hydrolysis further comprises an additional hydrolytic enzyme.

23. The method according to claim 19, wherein the first and second RNA-containing probes are blocked to extension at the 3' end.

24. The method according to claim 19, wherein the polymerase chain reaction is conducted in the presence of an alternative form of dATP, which, although acting as a substrate for DNA polymerisation, does not have any significant activity in the bioluminescent signalling system.

25. The method according to claim 24, wherein the alternative form of dATP is 2'-deoxyadenosine-5'-0-1-thiotriphosphate (dATPαS) or 7-deaza-2'-deoxyadenosine-5'-triphosphate (c7dATP).

26. The method according to claim 19, wherein the bioluminescent signalling system is added at the end of the amplification reaction.

27. The method according to claim 19, wherein the bioluminescent signalling system is added at the end of each cycle and the signal produced is read at that time.

28. The method according to claim 1, wherein the first nucleic acid is a target molecule, and the second nucleic acid is an internal control molecule which is added to the reaction mixture.

29. A method for detecting a nucleic acid sequence, said method comprising:
conducting a polymerase chain reaction in the presence of (a) a first RNA-containing probe which is capable of hybridising to a first nucleic acid during an annealing phase of the polymerase chain reaction, and a second RNA-containing probe which is capable of hybridising to a second nucleic acid also during the annealing phase of the polymerase chain reaction, wherein at least one adenosine in said first or said second RNA-containing probe is a modified form of adenosine, (b) an enzyme or enzyme mixture which hydrolyses the RNA-containing probes bound to the nucleic acids to generate adenosine monophosphate and/or modified adenosine monophosphate and (c) one or more enzymes or reagents necessary to convert adenosine monophosphate (AMP) to adenosine triphosphate (ATP) or modified adenosine monophosphate (AMP$^m$) to modified adenosine triphosphate (ATP$^m$);
phosphorylating any AMP and AMP$^m$ present to produce ATP or ATP$^m$ respectively;
adding to the sample bioluminescent reagents which produce a different signal in the presence of ATP as compared to ATP$^m$ and
determining the nature of the signal so produced and relating this to the presence of said first nucleic acid and said second nucleic acid in the sample.

30. A method for determining the sequence of a nucleic acid, said method comprising:
(i) binding a first and a second RNA-containing probe to a known region of said nucleic acid such that at least one nucleotide at an end of said probes reaches into an unknown region of the nucleic acid and wherein the first and second RNA-containing probes differ by the nucleotide found at the said end thereof, and wherein at least one adenosine in said first or said second RNA-containing probe is a modified form of adenosine;
(ii) hydrolysing the RNA-containing probes to generate adenosine monophosphate (AMP) and/or modified adenosine monophosphate (AMP$^m$) using an enzyme which hydrolyses said RNA-containing probes when in double stranded form;
(iii) converting AMP to adenosine triphosphate (ATP) and AMP$^m$ to modified adenosine triphosphate (ATP$^m$);
(iv) adding to the sample bioluminescent reagents which produce a different signal in the presence of ATP or ATP$^m$;
(v) detecting the signal from said bioluminescent reagents; and
(vi) relating that signal to the presence of a region of the nucleic acid which is complementary to the end of one of the said probes.

31. The method according to claim 30 which is carried out using four RNA-containing probes, each with a different nucleotide at an end thereof, and each containing a different form of adenosine.

32. The method according to claim 31, wherein in step (iii), the conversion is effected by adding phosphoenolpyruvate synthase, phosphate and phosphoenolpyruvate.

33. The method according to claim 31, wherein in step (iii), the conversion is effected by a combination of a nucleoside triphosphate-adenylate kinase, nucleoside 5'-triphosphate (NTP) and adenylate kinase.

34. The method according to claim 31, wherein said bioluminescent reagents used in step (iv) comprise luciferin and luciferase.

35. A method for detecting a nucleic acid in a sample, said method comprising:

contacting said sample with an RNA-containing probe that is capable of hybridising to the nucleic acid, the probe comprising an RNA/DNA heteropolymer which contains at least one adenosine or a modified form of adenosine under conditions such that the said RNA-containing probe will bind to any target nucleic acid present in the sample, subjecting any nucleic acid/probe complex to conditions under which the RNA-containing probe bound to nucleic acid is hydrolysed to generate adenosine monophosphate (AMP) or modified adenosine monophosphate (AMP'''), phosphorylating any AMP or AMP''' to produce adenosine triphosphate (ATP) or modified adenosine triphosphate (ATP''') respectively, detecting ATP or ATP''' using a bioluminescent signaling system.

\* \* \* \* \*

UNITED STATES PATENT AND TRADEMARK OFFICE
CERTIFICATE OF CORRECTION

| | | |
|---|---|---|
| PATENT NO. | : 7,838,236 B2 | Page 1 of 1 |
| APPLICATION NO. | : 12/064103 | |
| DATED | : November 23, 2010 | |
| INVENTOR(S) | : David James Squirrell | |

It is certified that error appears in the above-identified patent and that said Letters Patent is hereby corrected as shown below:

Claim 11, col. 15, line 8: "hosphorylating" should read --phosphorylating--

Signed and Sealed this
Second Day of August, 2011

David J. Kappos
*Director of the United States Patent and Trademark Office*